US006601439B2

United States Patent
Choikhet

(10) Patent No.: US 6,601,439 B2
(45) Date of Patent: Aug. 5, 2003

(54) METHOD OF REDUCING BASELINE INSTABILITIES IN LIQUID CHROMATOGRAPHIC MEASUREMENTS AND LIQUID CHROMATOGRAPHY APPARATUS

(75) Inventor: Konstantin Choikhet, Karlsruhe (DE)

(73) Assignee: Agilent Technologies, Inc., Palo Alto, CA (US)

( * ) Notice: Subject to any disclaimer, the term of this patent is extended or adjusted under 35 U.S.C. 154(b) by 26 days.

(21) Appl. No.: 09/907,365

(22) Filed: Jul. 17, 2001

(65) Prior Publication Data

US 2003/0005753 A1 Jan. 9, 2003

(30) Foreign Application Priority Data

Jul. 5, 2001 (EP) .............................. 01116298

(51) Int. Cl.⁷ ..................... G01N 30/54; B01D 15/08
(52) U.S. Cl. ................. 73/61.57; 73/61.55; 73/1.34; 95/87; 210/656
(58) Field of Search .............. 73/61.57, 61.55, 73/1.34, 23.23; 95/87; 210/656

(56) References Cited

U.S. PATENT DOCUMENTS

| 3,522,725 | A | * | 8/1970 | Waters | 73/61.1 |
|---|---|---|---|---|---|
| 4,019,372 | A | * | 4/1977 | Parkell et al. | 73/61.1 C |
| 4,312,835 | A | * | 1/1982 | Zoltan et al. | 422/70 |
| 4,814,089 | A | * | 3/1989 | Kumar | 210/659 |
| 4,927,532 | A | * | 5/1990 | Pospisil et al. | 210/198.2 |
| 4,966,695 | A | * | 10/1990 | Joshua | 210/198.2 |
| 4,994,096 | A | * | 2/1991 | Klein et al. | 55/20 |
| 5,135,549 | A | * | 8/1992 | Phillilps et al. | 55/67 |
| 5,543,315 | A | * | 8/1996 | Sugiyama et al. | 436/161 |
| 5,983,710 | A | | 11/1999 | Uhen et al. | 73/61.52 |
| 6,209,386 | B1 | * | 4/2001 | Mustacich et al. | 73/23.39 |
| 6,311,544 | B1 | * | 11/2001 | Bertrand | 73/23.35 |
| 6,484,569 | B1 | * | 11/2002 | Plant et al. | 73/61.57 |

FOREIGN PATENT DOCUMENTS

| DE | 91 14 773.5 | 2/1992 | |
|---|---|---|---|
| JP | 40-4-301763 A | * 10/1992 | .......... G01N/30/26 |
| JP | 2000111536 | 4/2000 | |

OTHER PUBLICATIONS

Muller, T. European Search Report, Applilcation Number EP 01 11 6298, dated Sep. 11, 2001.
Hayakawa Kazuichi et al. "Determination of saccharides in sake by high–performance liquid chromatography with polarized photometric detection." Database Biosis, Biosciences Information Service, Database accession no. PREV200000168864, Xp002176523, abstract.
Mayr, G. and Welsch, T. "Influence of viscous heat dissipation on efficiency in high–speed high–performance liquid chromatography." Journal of Chromatography A, Elsevier Science, NL, vol. 845, no. 1–2, Jun. 11, 1999, pp. 155–163.

* cited by examiner

Primary Examiner—Helen Kwok
Assistant Examiner—David J. Wiggins

(57) ABSTRACT

A method of reducing baseline instabilities in liquid chromatographic measurements is disclosed. A mobile phase comprising sample substances passes through a chromatographic column comprising a stationary phase, and subsequently through a detector. An additional solid body or liquid bath having a high heat capacity and heat conductance is coupled to the column and to an inlet capillary of the column such that the inlet capillary and the column are enclosed by said solid body or liquid bath. In that way temperature stabilization of the column and inlet capillaries is achieved and baseline variations due to temperature dependent adsorption of water at the stationary phase, in particular stationary phases with amino functional groups, are reduced.

13 Claims, 4 Drawing Sheets

METHOD OF REDUCING BASELINE INSTABILITIES IN LIQUID CHROMATOGRAPHIC MEASUREMENTS AND LIQUID CHROMATOGRAPHY APPARATUS

FIELD OF THE INVENTION

The invention relates to a method of improving baseline stability in liquid chromatographic measurements and to a liquid chromatography apparatus having means for reducing baseline instabilities.

BACKGROUND OF THE INVENTION

High performance liquid chromatography is a separation technique wherein a mixture of sample substances dissolved in a solvent (mobile phase) is forced under high pressure through a separation column. Different sample substances interact differently with the stationary phase in the column and therefore elute from the column at different times. The separated sample substances leaving the column are detected with a suitable detector, such as an absorbance detector, refractive index detector, conductivity detector, or electrochemical detector. The representation of the detector signal as a function of time is called chromatogram. Different sample substances are represented by individual peaks in the chromatogram; the peak area is a measure of the amount of the corresponding sample substance.

In order to ensure reproducible measurements, in particular quantitative measurements, it is important that the baseline in the chromatogram remains stable, i.e. that it is not affected by influences which have nothing to do with the sample substances. A varying baseline would interfere with the chromatographic peaks and thus lead to incorrect measuring results. In particular refractive index detectors are very sensitive to instrumental and external influences leading to unwanted baseline variations. For example, high pressure pumps forcing the solvent and sample through the column often generate pressure pulsations which can lead to refractive index signal changes which in turn are causing artefacts in the measuring signal.

A new type of baseline instability has been observed by the inventor of the present invention, in particular in connection with stationary phases comprising amino functional groups. Columns of this type are used, for example, for sugar analysis. The observed baseline instabilities occur in the form of "wander" in the time range of 1–10 minutes and can thus easily interfere with chromatographic peaks.

SUMMARY OF THE INVENTION

It is thus an object of the present invention to provide a method and a corresponding apparatus for reducing the mentioned baseline variations.

It is a further object of the invention to provide a liquid chromatography apparatus having improved baseline stability.

According to the invention, these objects are achieved by for a method by claim 1 and for an apparatus by claim 9.

The invention according to claim 1 is based on the surprising finding that the baseline variation originates from variations in the adsorption of water (or one of the eluent components) to the stationary phase and that this adsorption is sensitive to temperature fluctuations. Thus, the amount of water in the mobile phase reaching the detector varies with temperature changes, leading to the baseline wander in the detector signal. The baseline problems are substantially reduced by coupling an additional solid body or liquid bath having a high heat capacity and heat conductance to the column and to an inlet capillary of the column such that the inlet capillary and the column are entirely enclosed by said solid body or liquid bath. The invention is particularly useful in connection with refractive index detection which is very sensitive to changes in the measuring conditions, but it is also advantageous for other detection methods, such as absorbance detection. It is understood that the invention is not only applicable for stationary phases with amino groups, but also for other types of stationary phases, e.g. reversed phases (RP) in connection with mobile phases containing UV absorbing additives which have a temperature dependent affinity to the stationary phase.

The invention also provides a general solution for temperature stabilization of the column, allowing a constancy of the column temperature of better than 0.001 degrees centigrade per minute. According to claim 9, an additional solid body or liquid bath having a high heat capacity and heat conductance, is coupled to the column and to an inlet capillary of the column such that the inlet capillary and the column are enclosed by said solid body or liquid bath. Preferably, the additional solid body and the inlet capillary are arranged in a thermostatted column compartment of the chromatograph which comprises a controlled heat source and/or heat sink. According to a preferred embodiment, the heat impedance between the additional solid body and the controlled heat source/sink is optimized to ensure that equilibration times do not become too long, and to avoid cross-talk of the small, fast fluctuations from the heat source/sink which would otherwise directly influence the column temperature.

BRIEF DESCRIPTION OF THE DRAWINGS

Subsequently, embodiments of the invention will be explained in detail with reference to the drawings.

DETAILED DESCRIPTION OF THE INVENTION

It has been observed by the inventor of the present invention that baseline wander occurs in liquid chromatographic measurements, in particular when using columns with stationary phases having amino functional groups and when the eluent leaving the column is detected with a refractive index detector. In a typical experiment, the stationary phase was a silica based packing coated with polymer resin containing secondary and tertiary amino functional groups. The mobile phase was a mixture of acetonitrile (ACN) and water. A disturbing baseline wander occurred at higher ACN concentrations, typically above 65%. This baseline wander occurred, even though the column was thermostatted as it is usual practice in liquid chromatographs.

Surprisingly, the inventor found out that the baseline wander has to do with variations in the adsorption of water to the stationary phase and that this adsorption is sensitive to temperature fluctuations. The water molecules in the mobile phase form hydrogen bonds with the amino groups of the stationary phase. These hydrogen bonds are very sensitive to temperature changes so that, depending on the temperature, more or less water molecules are released into the solvent and subsequently cause a corresponding detector signal. In particular refractive index detectors are sensitive to such changes of the water concentration.

Figure 1:
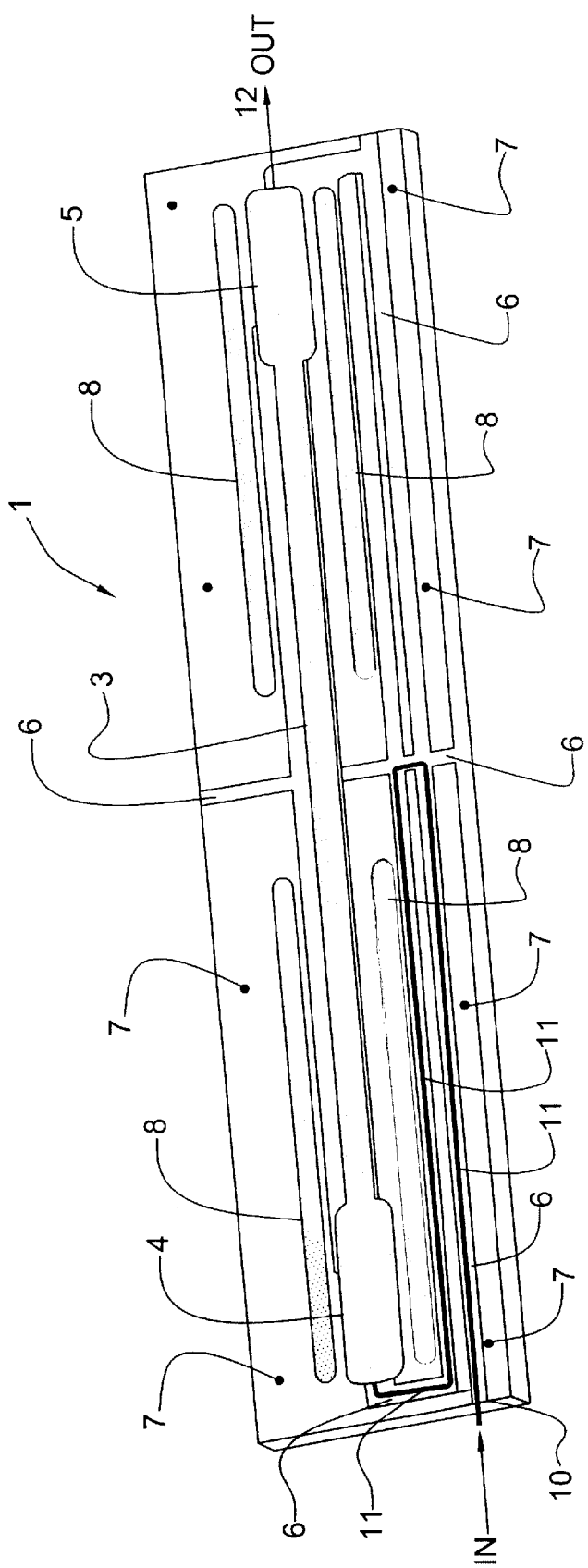
FIG. 1 shows a part of the metal block to be coupled to the column, according to an embodiment of the invention.

The present invention provides a simple means to substantially reduce the mentioned problems. FIG. 1 illustrates a first embodiment. A solid metal body 1 is arranged inside the thermostated column compartment of a liquid chromatograph, for example the Agilent Technologies Series 1100 liquid chromatograph. The metal body 1 comprises an elongated recess 3 for receiving the column (not shown). The widened recess portions 4, 5 serve for accommodating the end fittings of the column. The body 1 also comprises grooves 6 for receiving the inlet and outlet capillaries of the column which are connected to the end fittings, respectively. The grooves 6 are folded several times and thus allow to accommodate a relatively great length of inlet capillary within the body 1. When the column and the capillaries have been inserted into the corresponding recesses, a second metal body (not shown) which is substantially the mirror image of the body 1 is arranged onto the body 1 such that the column and the capillaries are enclosed by the two bodies. The two bodies may be connected with screws via screw holes 7.

The metal body is made of a material which has a high heat capacity and a high heat conductance, such as aluminum. The body has typical dimensions of about 33 cm×7 cm×2 cm, wherein the latter dimension applies for the two bodies when joined together. The inlet capillary to the column which is typically made of steel is jammed in the grooves 6 such that it is in good heat contact with the surrounding metal. Typically, about 30 cm or more of the inlet capillary are arranged in the metal body. In the embodiment of FIG. 1, the inlet capillary enters the metal block 1 at reference numeral 10 and follows the path in the grooves 6 illustrated by the solid line 11 and after a few turns enters the column. The outlet capillary leaves the column at position 12. The outer diameter of the inlet capillary and of the outlet capillary is about 0.8 mm. The column is either jammed in the groove 3 or is hanging freely in a cavity larger than the column itself.

As already mentioned, the metal body 1 with its complementary counterpart and the enclosed column as well as inlet and outlet capillaries are arranged inside the thermostatted column compartment and it substantially fills out the space of the compartment. The thermostat arrangement inside the compartment comprises a heat exchanger with heat exchanger fins which project into slit openings 8 of the body 1. There is no direct contact between the heat exchanger and the body 1, a distance of 1 to 2 mm is maintained everywhere, for example by non-heat conducting spacers. The heat exchanger allows to adjust a desired temperature in the column compartment for a specific chromatographic separation by appropriate heating/cooling means and corresponding control circuitry. Additional heat insulating material is placed in the column compartment around the sides of the metal body not directed to the heat exchanger surfaces. This reduces ambient effects by increasing the heat impedance from ambient to the metal block.

The distance between the metal body and the heat exchanger ensures an optimum heat impedance between the two. The additional heat capacity coupled to the mobile phase entering the column contributes to the smoothing of temperature fluctuations. If the column is jammed into the metal body, it is also coupled to the additional heat capacity; if the column is hanging freely inside of the essentially isothermal chamber in the metal body, it is shielded from ambient effects by the highly heat conductive metal body. Since the flow path from the point of the inlet capillary entering the metal body up to the column outlet capillary is entirely enclosed inside the metal body, ambient effects are excluded all over the relevant part of the flow path. The mobile phase heating due to mechanical losses (hydraulic friction) within the column is either negligible or anyway stationary.

Figure 2:
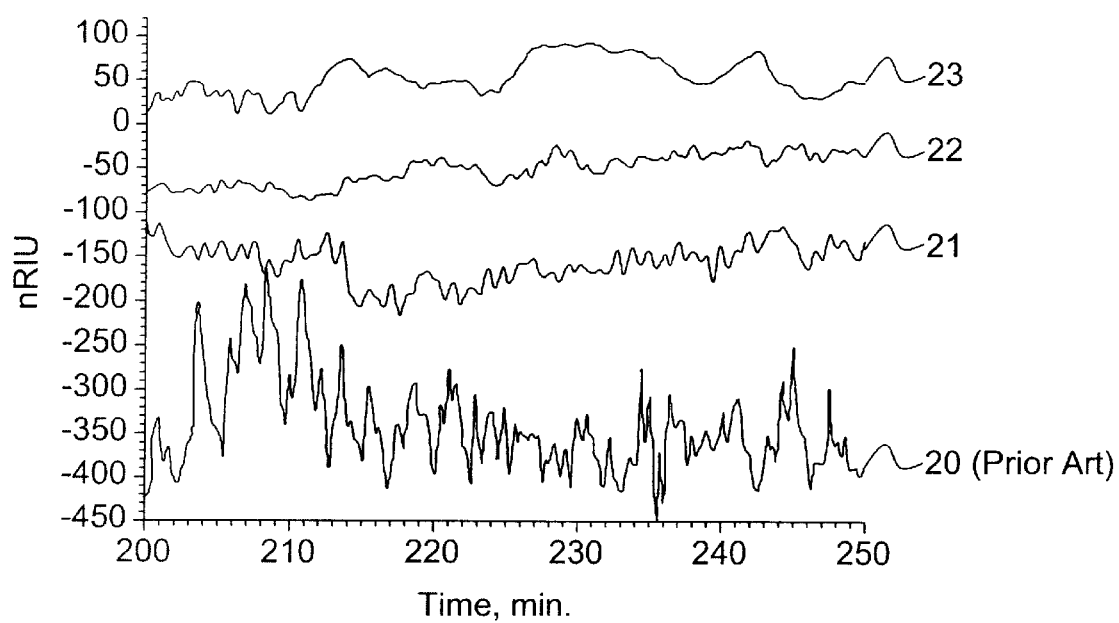
FIG. 2 is a graphical representation of baseline vs. time for various embodiments of the invention compared to the prior art.

FIG. 2 illustrates the improvements in baseline stability which are achieved with the present invention. It shows the output signal of a refractive index detector (in nano refractive index units) coupled to the liquid chromatograph as a function of time. The curve 20 shows the baseline variation in a conventional set-up wherein the column is arranged in a thermostat. Curve 21 shows the baseline variation in an embodiment of the invention wherein the column is in intimate contact with an aluminum body, i.e. wherein the recess for the column has the same diameter as the column tube. The heat exchanger fins are close to the aluminum body, i.e. the slits 8 of the body are about 1 mm wider than the fins so that the body surface is sitting directly on the fins or has a distance of max. 0.5 mm from the fins. In the embodiment illustrated with curve 22 the column is in intimate contact with the aluminum body as in the previous embodiment, but the surfaces of the heat exchanger fins are at a distance of 1.5 mm from the body, i.e. the slits 8 are about 3 mm wider than the fins and the aluminum body is sitting on rubber strips over the fins. In the embodiment illustrated with curve 23 the column has no immediate contact with the aluminum body, but it is enclosed by it. As in the previous embodiment (curve 22), the heat exchanger fins surfaces are at a distance of 1.5 mm from the aluminum body.

The invention also provides a general solution for the problem of disturbing heat flows originating from various sources, such as (a) ambient influences, (b) temperature fluctuations in the mobile phase entering the column, (c) active temperature regulation by the thermostat. Furthermore, the invention reduces the ambient cross-talk on the temperature of the column and of the mobile phase.

Expressed in terms of an analogous electrical circuitry, the invention smoothes the fluctuations by means of a low-pass filter, and the ambient cross-talk is reduced by placing the critical system parts into a shielded space, e.g. in a chamber with the walls being maintained at a constant temperature level.

Figure 3:
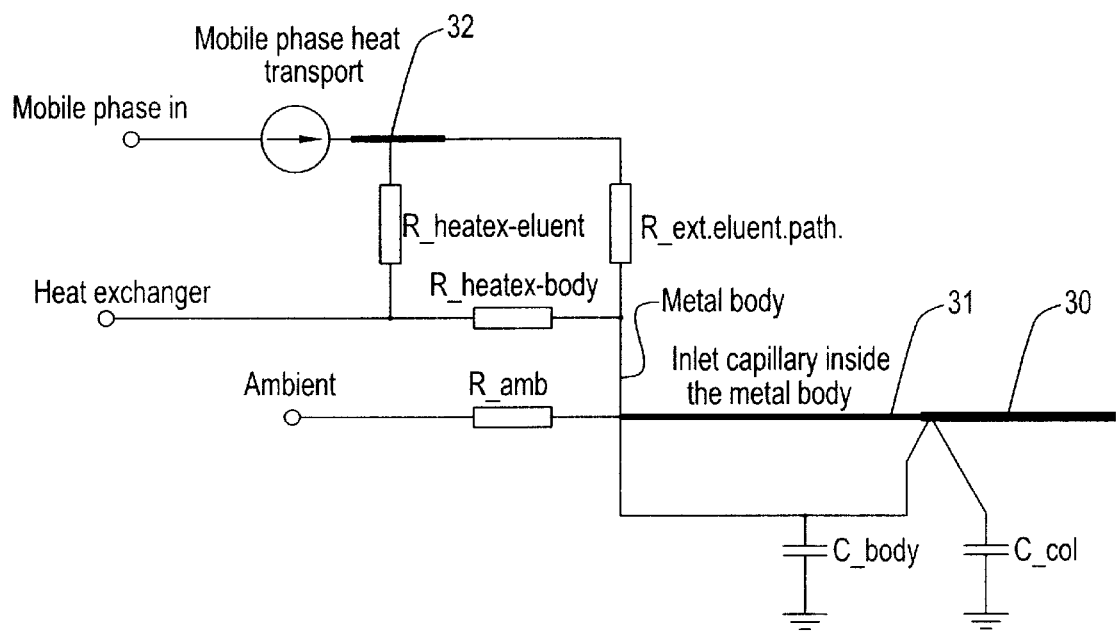
FIG. 3 is an equivalent circuit diagram illustrating an embodiment of the invention.
Figure 4:
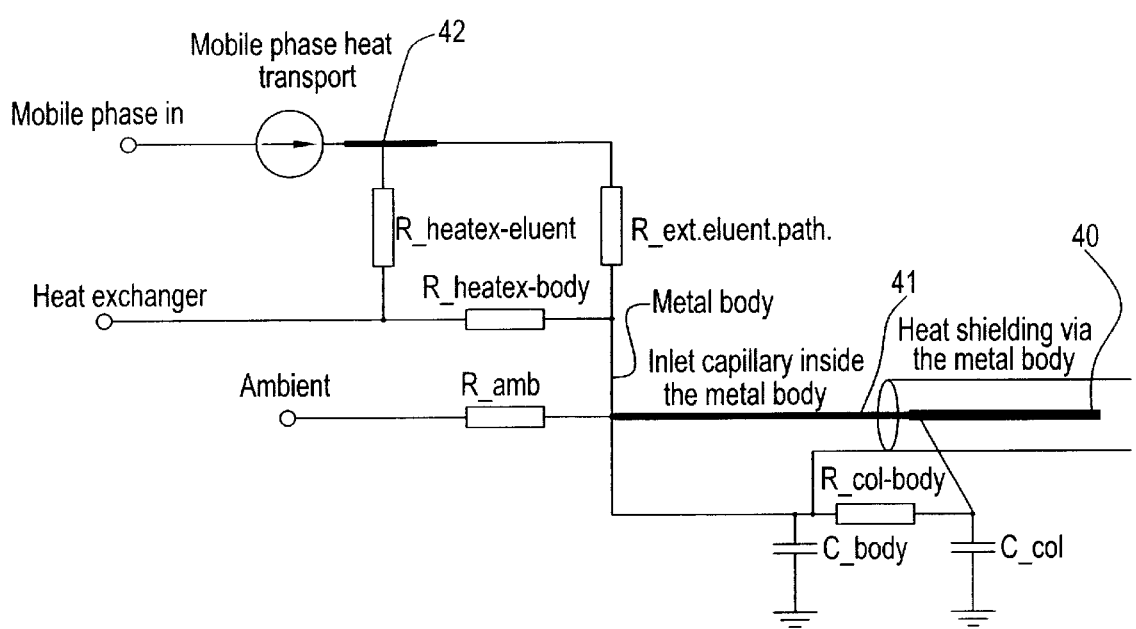
FIG. 4 is an equivalent circuit diagram illustrating another embodiment of the invention.

In the following two embodiments of the invention will be explained with reference to equivalent electric circuits which are shown in FIGS. 3 and 4. FIG. 3 illustrates the case wherein the column 30 is in direct contact with the metal body 1, and FIG. 4 illustrates the case wherein the column 40 is hanging freely in the cavity within the metal body. The heat flow sources in both systems are:

- the mobile phase flow, i.e. heat transport coupled with mass transport,
- the heat exchanger which is actively driven,
- heat flows from ambient.

The heat flows due to the heat exchanger and the heat flows from ambient directly influence the metal body via the impedances R_heatex-body and R_amb, as shown in FIGS. 3 and 4. The heat flow transported with the mobile phase (eluent) is coming predominantly from the heat exchanger via the low impedance R_heatex-eluent as the mobile phase passes through the heat exchanger capillary. The portion of the inlet capillary inside the heat exchanger is illustrated in FIGS. 3 and 4 with reference numerals 32 and 42, respectively. The heat flow transported with the mobile phase is additionally changed in the free part of the inlet capillary, illustrated with R_ext.eluent.path. The temperature fluctuations of the environment of the metal body and of the inlet capillary coupled to it (reference numerals 31,41) are then smoothed by the low-pass filter formed by the heat capacity of the metal body C_body and by the impedances R_heatex-body and R_amb. In FIG. 3 the heat capacity of the column C_col is then connected in parallel to the heat capacity C_body of the metal body participating in the mentioned RC filter. In FIG. 4 the column 40 is shielded from external heat disturbances by the isothermal walls of the cavity inside the metal block surrounding the column. The impedance R_col-body between the walls of the cavity and the column forms, together with the capacity C_col an additional RC filter.

In concrete implementations of the arrangements shown in FIGS. 3 and 4, it has to be ensured that there is good direct thermal contact of the inlet capillary 31, 41 to the metal body. The metal body should be thermally insulated against ambient heat flows. Furthermore, the heat impedance between the active thermostat of the chromatograph and the metal body should be optimized. If the selected impedance were too high, this would result in too long temperature equilibration times and significant temperature differences between the thermostat and the metal body due to ambient heat flows. If the impedance were too low, this would eliminate any temperature smoothing effect and result in direct cross-talk of the temperature fluctuation generated by the active regulation in the thermostat onto the column. As an additional design criterion, the entire section of the mobile phase flow path from the inlet capillary up to the end of the column should be entirely enclosed within the metal body such that there is no contact to the outside of the metal body.

It is understood that the additional heat capacity can not only be provided in the form of a solid metal body (e.g., aluminum, copper), but also in the form of metal wool or filings, or as a liquid bath, with high heat capacity and high heat conductance. The additional heat capacity should be substantially greater than the heat capacity of the column. According to a practical example, the heat capacity of the metal body is about 10 to 20 times greater than the heat capacity of the column. The heat conductance should also be high, in order to ensure that the heat flow oscillations propagate and are averaged over the whole metal body in a time shorter than the characteristic fluctuation time, thus ensuring participation of the entire additional heat capacity in the smoothing.

The invention is particularly suited for use in connection with refractive index detectors which are very sensitive to changes in the measuring conditions, such as composition and temperature of the mobile phase. The advantages of the invention, however, also apply with other types of detectors, such as absorbance detectors.

What is claimed is:

1. A method of reducing baseline instabilities in liquid chromatographic measurements wherein a mobile phase comprising sample substances passes through a chromatographic column comprising a stationary phase, and wherein the mobile phase subsequently passes through a detector, and wherein an additional solid body or liquid bath having a high heat capacity and high heat conductance is coupled to the column and to an inlet capillary of the column such that the inlet capillary and the column are enclosed by said solid body or liquid bath; said method serves to minimize the effect of temperature dependent water adsorbed at said stationary phase.

2. A method as in claim 1, wherein the stationary phase comprises amino functional groups.

3. A method as in claim 1, wherein the mobile phase comprises water.

4. A method as in claim 3, wherein the mobile phase additionally comprises acetonitrile.

5. A method as in claim 1, used in sugar analysis.

6. A method as in claim 1, wherein the detector is a refractive index detector.

7. A method as in claim 1, wherein the column, the inlet capillary and the additional solid body or liquid bath are arranged in a thermostatted column compartment comprising a controlled heat source and/or heat sink.

8. A method as in claim 7, wherein the heat impedance between the additional solid body or liquid bath on the one hand and the controlled heat source and/or heat sink on the other hand is optimized to ensure that equilibration times do not become too long and to avoid cross-talk from the heat source/sink which would disturb the smoothing effect of the additional solid body and/or liquid bath.

9. A liquid chromatography apparatus comprising:
 a chromatographic column with a stationary phase,
 means to drive a mobile phase comprising sample substances through the column,
 a detector for detecting sample substances leaving the chromatographic column, and
 means for reducing baseline instabilities comprising:
  an additional solid body or liquid bath having a high heat capacity and heat conductance, coupled to the column and to an inlet capillary of the column such that the inlet capillary and the column are enclosed by said solid body or liquid bath; said means for reducing baseline instabilities minimizes the effect of temperature dependent water adsorbed at said stationary phase.

10. Apparatus as in claim 9, wherein a thermostatted column compartment comprising a controlled heat source and/or heat sink is provided, and that the inlet capillary and the additional solid body or liquid bath are arranged in said thermostatted compartment.

11. Apparatus as in claim 10, wherein the heat impedance between the additional solid body or liquid bath on the one hand and the controlled heat source and/or heat sink on the other hand is optimized to ensure that equilibration times do not become too long, and to avoid cross-talk from the heat source which would disturb the smoothing effect of the additional solid body and/or liquid bath.

12. Apparatus as in claim 9, wherein the detector is a refractive index detector.

13. Apparatus as in claim 9, wherein the stationary phase comprises amino functional groups.

* * * * *